US011311722B2

(12) United States Patent
Shazly et al.

(10) Patent No.: US 11,311,722 B2
(45) Date of Patent: *Apr. 26, 2022

(54) CROSS-PLATFORM WORKLOAD PROCESSING

(71) Applicant: International Business Machines Corporation, Armonk, NY (US)

(72) Inventors: Hassan A. Shazly, Columbia, SC (US); Douglas A. Van Dyken, Anderson, SC (US)

(73) Assignee: International Business Machines Corporation, Armonk, NY (US)

( * ) Notice: Subject to any disclaimer, the term of this patent is extended or adjusted under 35 U.S.C. 154(b) by 315 days.

This patent is subject to a terminal disclaimer.

(21) Appl. No.: 15/812,827

(22) Filed: Nov. 14, 2017

(65) Prior Publication Data

US 2018/0064936 A1 Mar. 8, 2018

Related U.S. Application Data

(63) Continuation of application No. 15/488,208, filed on Apr. 14, 2017, now abandoned, which is a
(Continued)

(51) Int. Cl.
*A61N 1/32* (2006.01)
*A61K 9/00* (2006.01)
(Continued)

(52) U.S. Cl.
CPC ............ *A61N 1/327* (2013.01); *A61K 9/0009* (2013.01); *A61K 38/14* (2013.01); *A61M 5/19* (2013.01); *A61M 5/20* (2013.01)

(58) Field of Classification Search
CPC ... G06F 9/505; G06F 9/5083; G06F 2209/503
See application file for complete search history.

(56) References Cited

U.S. PATENT DOCUMENTS 6,249,836 B1  6/2001  Downs et al.
6,449,707 B1  9/2002  Gotou
(Continued)

FOREIGN PATENT DOCUMENTS

JP   03233637      10/1991
JP   H03233637   * 10/1991
(Continued)

OTHER PUBLICATIONS

Ejarque, Jorge, et al. "Semantic resource allocation with historical data based predictions" (2010), The First International Conference on Cloud Computing, GRIDs, and Virtualization pp. 104-109. (Year: 2010).*

(Continued)

*Primary Examiner* — Meng Ai T An
*Assistant Examiner* — Willy W Huaracha
(74) *Attorney, Agent, or Firm* — Alex Harvey

(57) ABSTRACT

A technique for workload processing includes receiving a request to process a workload by a scheduler. A determination is made whether multiple stages of processing are needed to process data of the workload. If so, a determination is made of a process needed for each stage and historical processing data is accessed to determine historical execution statistics associated with previous processing requests for a corresponding type of the workload. At each stage, a determination is made whether the data of the workload is available for processing and, if so, whether the respective process of the workload is available. If available, a determination is made as to resource availability on a computing platform for processing the workload and whether the resources available are sufficient to process the workload based on the historical execution statistics. If sufficient resources are available, processing of the workload is initiated for the respective stage.

15 Claims, 6 Drawing Sheets

Related U.S. Application Data continuation of application No. 14/099,993, filed on Dec. 8, 2013, now Pat. No. 9,652,294, which is a continuation of application No. 14/088,708, filed on Nov. 25, 2013, now Pat. No. 9,626,226.

(51) Int. Cl.
*A61K 38/14* (2006.01)
*A61M 5/19* (2006.01)
*A61M 5/20* (2006.01)

(56) References Cited

U.S. PATENT DOCUMENTS

| | | | | |
|---|---|---|---|---|
| 6,772,395 | B1* | 8/2004 | Hyman | G06F 40/14 |
| | | | | 715/234 |
| 7,644,148 | B2 | 1/2010 | Ranganathan et al. | |
| 7,860,897 | B2 | 12/2010 | Dettinger et al. | |
| 7,958,511 | B1 | 6/2011 | Pomerantsev et al. | |
| 8,046,763 | B1* | 10/2011 | Czajkowski | G06F 9/5011 |
| | | | | 718/104 |
| 8,689,226 | B2 | 4/2014 | Cipar et al. | |
| 8,793,381 | B2* | 7/2014 | Baughman | G06F 9/5083 |
| | | | | 709/226 |
| 9,015,724 | B2 | 4/2015 | Druyan | |
| 9,047,141 | B2* | 6/2015 | Malewicz | G06F 7/38 |
| 9,513,967 | B2 | 12/2016 | Dube et al. | |
| 2002/0129085 | A1 | 9/2002 | Kubala et al. | |
| 2005/0076043 | A1 | 4/2005 | Benedetti et al. | |
| 2007/0143765 | A1 | 6/2007 | Aridor et al. | |
| 2009/0158288 | A1* | 6/2009 | Fulton | G06F 9/4881 |
| | | | | 718/103 |
| 2009/0228821 | A1 | 9/2009 | Tapper | |
| 2009/0235274 | A1* | 9/2009 | Uruma | G06F 9/4881 |
| | | | | 718/107 |
| 2010/0153431 | A1 | 6/2010 | Burger | |
| 2011/0060757 | A1* | 3/2011 | Dettinger | G16H 10/60 |
| | | | | 707/769 |
| 2011/0072437 | A1* | 3/2011 | Druyan | G06F 9/505 |
| | | | | 718/104 |
| 2011/0302587 | A1* | 12/2011 | Nishikawa | G06F 9/4881 |
| | | | | 718/103 |
| 2011/0311043 | A1* | 12/2011 | Sibert | H04W 12/0013 |
| | | | | 380/31 |
| 2012/0054770 | A1* | 3/2012 | Krishnamurthy | G06F 9/4893 |
| | | | | 718/105 |
| 2012/0054771 | A1 | 3/2012 | Krishnamurthy et al. | |
| 2012/0192188 | A1* | 7/2012 | Ferdous | G06F 9/5044 |
| | | | | 718/101 |
| 2012/0198466 | A1 | 8/2012 | Cherkasova et al. | |
| 2012/0291041 | A1* | 11/2012 | Cipar | G06F 9/5011 |
| | | | | 718/104 |
| 2012/0317069 | A1* | 12/2012 | Oono | G06F 11/3419 |
| | | | | 706/47 |
| 2012/0324092 | A1* | 12/2012 | Brown | G06F 9/5044 |
| | | | | 709/224 |
| 2013/0061233 | A1* | 3/2013 | Zhou | G06F 9/4881 |
| | | | | 718/103 |
| 2013/0104136 | A1 | 4/2013 | Brech et al. | |
| 2013/0239112 | A1* | 9/2013 | Kato | G06F 9/5077 |
| | | | | 718/1 |
| 2014/0007121 | A1* | 1/2014 | Caufield | G06F 9/4843 |
| | | | | 718/103 |
| 2015/0199218 | A1 | 7/2015 | Wilson et al. | |
| 2016/0224385 | A1* | 8/2016 | Ichikawa | G06T 1/20 |
| 2018/0352557 | A1* | 12/2018 | Bhatt | G06F 3/0659 |

FOREIGN PATENT DOCUMENTS

| | | |
|---|---|---|
| JP | 2005508033 | 3/2005 |
| JP | 2007128356 | 5/2007 |
| JP | 2008305004 | 12/2008 |
| JP | 2010165259 | 7/2010 |
| WO | 2012127641 | 9/2012 |

OTHER PUBLICATIONS

Ebbers, Mike, et al.; Addressing Data Volume and Variety with IBM InfoSphere Streams V3.0; IBM Redbook; IBM International Technical Support Organization; Mar. 2013.

Gucer, Vasfi, et al.; IBM Tivoli Workload Scheduler for z/OS Best Practices—End-to-end and mainframe scheduling; IBM Redbook; IBM International Technical Support Organization; May 2006.

Castro, Sofia, et al.; AIX 5L Workload manager (WLM); IBM Redbook; IBM International Technical Support Organization; Jun. 2001.

International Preliminary Report on Patentability; International Application No. PCT/JP2014/004925; dated May 31, 2016.

International Search Report and Written Opinion; International Application No. PCT/JP2014/004925; dated Jan. 6, 2015.

* cited by examiner

CROSS-PLATFORM WORKLOAD PROCESSING

BACKGROUND

One goal in distributed and other types of computing environments is to maximize throughput of large numbers of related workloads. One technique used to address the foregoing is time-based scheduling (i.e., scheduling the times when each of the workloads should execute). Another technique is sequence-based scheduling (i.e., scheduling a sequence in which the workloads should execute). Priority-based scheduling may also be used (i.e., running the workloads based on CPU availability and workload priority). Despite these techniques, there may be delays or other conditions that may adversely affect throughput of the workload.

BRIEF SUMMARY

According to one aspect of the present disclosure a method and technique for workload processing is disclosed. The method includes receiving a request to process a workload by a scheduler. A determination is made whether multiple stages of processing are needed to process data of the workload. If so, a determination is made of a process needed for each stage and historical processing data is accessed to determine historical execution statistics associated with previous processing requests for a corresponding type of the workload. At each stage, a determination is made whether the data of the workload is available for processing and, if so, whether the respective process of the workload is available. If the data and the process are available, a determination is made as to resource availability on a computing platform for processing the workload and whether the resources available are sufficient to process the workload based on the historical execution statistics. If sufficient resources are available, processing of the workload is initiated for the respective stage.

BRIEF DESCRIPTION OF THE SEVERAL VIEWS OF THE DRAWINGS

For a more complete understanding of the present application, the objects and advantages thereof, reference is now made to the following descriptions taken in conjunction with the accompanying drawings, in which.

DETAILED DESCRIPTION

Figure 1:
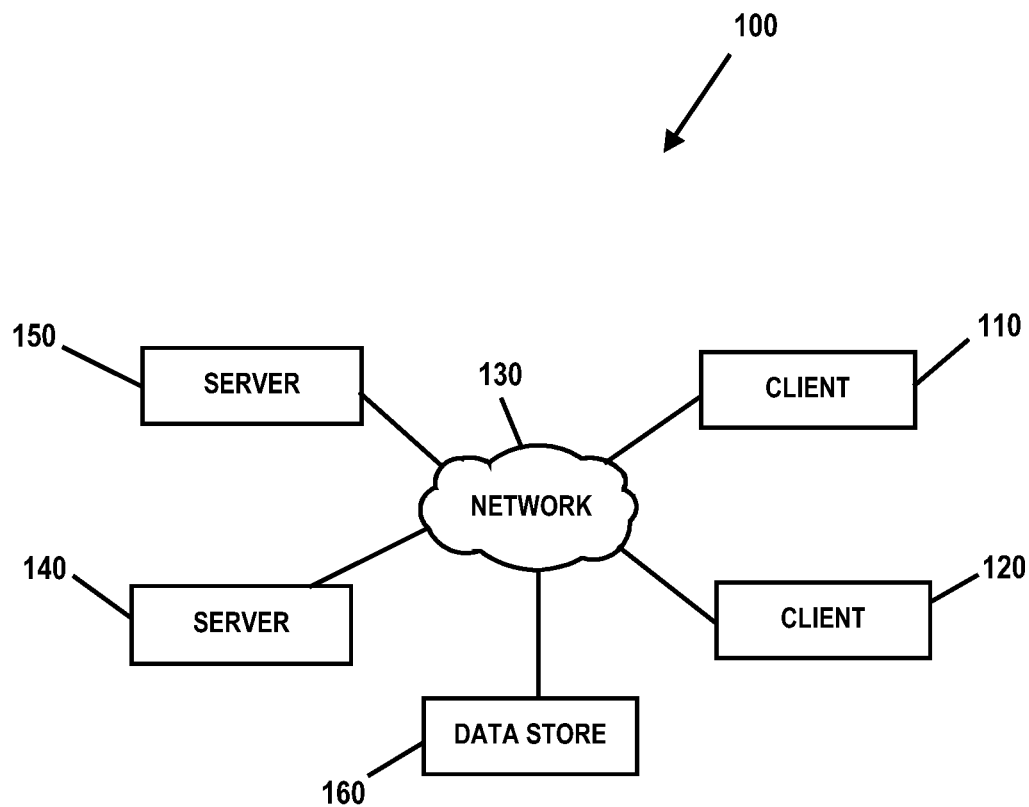
FIG. 1 is an embodiment of a network of data processing systems in which the illustrative embodiments of the present disclosure may be implemented.

Embodiments of the present disclosure provide a method, system and computer program product for cross-platform workload processing. For example, in some embodiments, the method and technique includes: receiving a request to process a workload by a scheduler executing on a processor unit; accessing historical processing data by the scheduler to determine execution statistics associated with previous processing requests; determining whether the data of the workload is available for processing; in response to determining that the data is available for processing, determining whether a process for the workload is available; in response to determining that the process is available, determining resource availability on a computing platform for processing the workload; determining whether excess capacity is available on the computing platform based on the resource availability and the execution statistics; and in response to determining that excess capacity exists on the computing platform, initiating processing of the workload on the computing platform. Thus, embodiments of the present disclosure enable workload throughput optimization using a knowledge base to evaluate throughput information obtained from previous, similar workload processing to efficiently schedule and manage workload processing across one or more computing platforms. A set of rules may be set/used to determine which workload (input data and process) is to be processed next, the availability of the workload, and on a priority determined by the knowledge base. A scheduler waits for the arrival/availability of processes and their related data and, in response to the data and its associated process(es) having arrived or otherwise being available, the workload is eligible to be submitted according to a priority of the workload (e.g., as set forth by the rules) and the availability of processing/execution resources. The scheduler controls/manages intermediate processing stages of the workload without user intervention based on the workload being available for processing as well as computing resource availability.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer usable or computer readable medium(s) may be utilized. The computer readable medium may be a computer readable signal medium or a computer readable storage medium. A computer readable storage medium may be, for example but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 2:
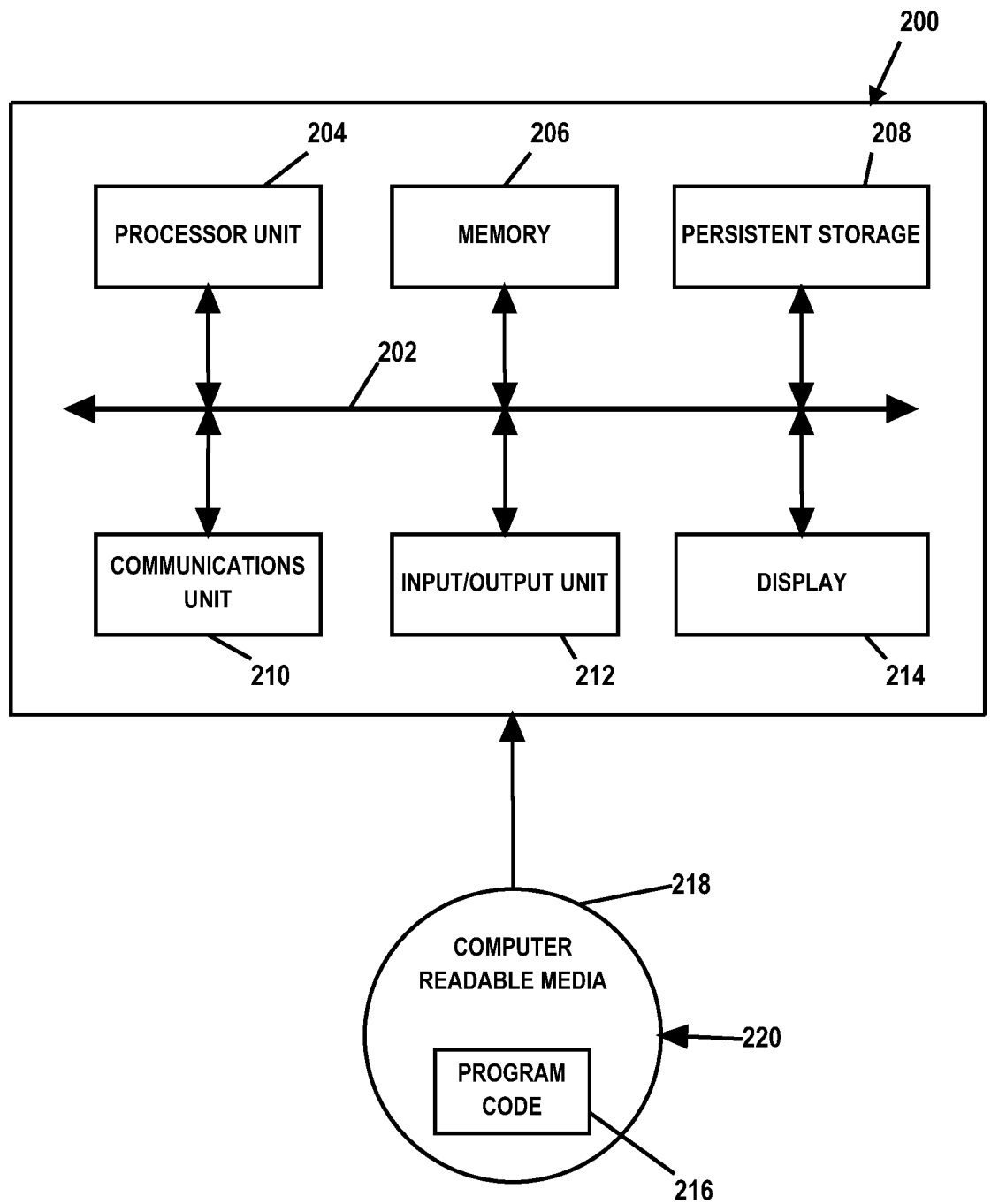
FIG. 2 is an embodiment of a data processing system in which the illustrative embodiments of the present disclosure may be implemented.

With reference now to the Figures and in particular with reference to FIGS. 1-2, exemplary diagrams of data processing environments are provided in which illustrative embodiments of the present disclosure may be implemented. It should be appreciated that FIGS. 1-2 are only exemplary and are not intended to assert or imply any limitation with regard to the environments in which different embodiments may be implemented. Many modifications to the depicted environments may be made.

FIG. 1 is a pictorial representation of a network of data processing systems in which illustrative embodiments of the present disclosure may be implemented. Network data processing system 100 is a network of computers in which the illustrative embodiments of the present disclosure may be implemented. Network data processing system 100 contains network 130, which is the medium used to provide communications links between various devices and computers connected together within network data processing system 100. Network 130 may include connections, such as wire, wireless communication links, or fiber optic cables.

In some embodiments, server 140 and server 150 connect to network 130 along with data store 160. Server 140 and server 150 may be, for example, IBM® Power Systems™ servers. In addition, clients 110 and 120 connect to network 130. Clients 110 and 120 may be, for example, personal computers or network computers. In the depicted example, server 140 provides data and/or services such as, but not limited to, data files, operating system images, and applications to clients 110 and 120. Network data processing system 100 may include additional servers, clients, and other devices.

In the depicted example, network data processing system 100 is the Internet with network 130 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

FIG. 2 is an embodiment of a data processing system 200 such as, but not limited to, client 110 and/or server 140 in which an embodiment of a system for cross-platform workload processing according to the present disclosure may be implemented. In this embodiment, data processing system 200 includes a bus or communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

In some embodiments, memory 206 may be a random access memory or any other suitable volatile or non-volatile storage device. Persistent storage 208 may take various forms depending on the particular implementation. For example, persistent storage 208 may contain one or more components or devices. Persistent storage 208 may be a hard drive, a flash memory, a rewritable optical disk, a rewritable magnetic tape, or some combination of the above. The media used by persistent storage 208 also may be removable such as, but not limited to, a removable hard drive.

Communications unit 210 provides for communications with other data processing systems or devices. In these examples, communications unit 210 is a network interface card. Modems, cable modem and Ethernet cards are just a few of the currently available types of network interface adapters. Communications unit 210 may provide communications through the use of either or both physical and wireless communications links.

Input/output unit 212 enables input and output of data with other devices that may be connected to data processing system 200. In some embodiments, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer readable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown. For example, a storage device in data processing system 200 is any hardware apparatus that may store data. Memory 206, persistent storage 208, and computer readable media 218 are examples of storage devices in a tangible form.

Figure 3:
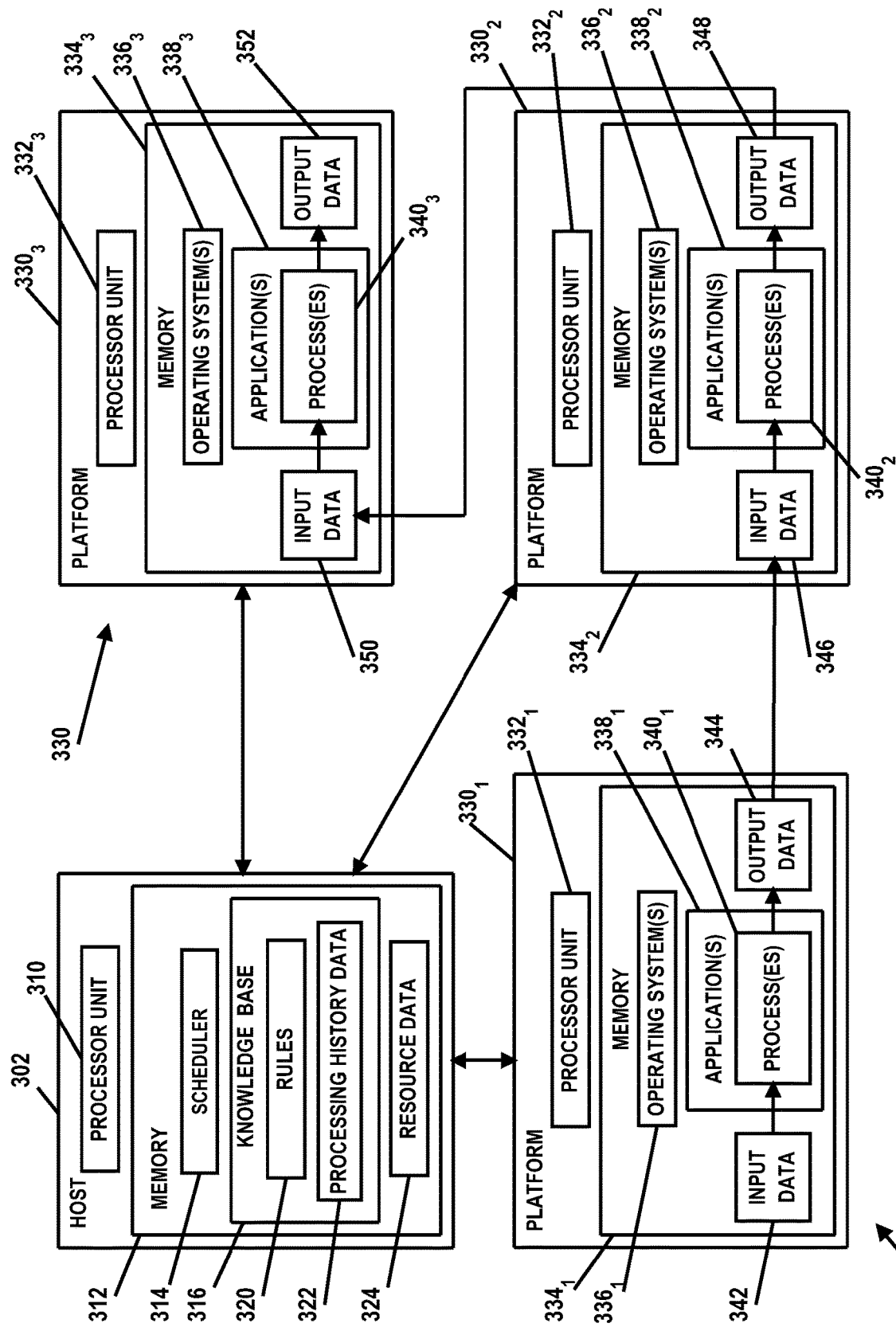
FIG. 3 is a diagram illustrating an embodiment of a computing environment in which illustrative embodiments of a cross-platform workload processing system according to the present disclosure may be implemented.

FIG. 3 is a diagram illustrating a computing environment in which an embodiment of a system 300 for cross-platform workload processing according to the present disclosure may be implemented. System 300 enables the throughput maximization of very large volumes of workloads using knowledge-based or learned information. The workloads may include data and their associated processes (programs/applications that will process the data). The data may be processed multiple times across one or more different computing platforms before the final output is created. The workload throughput is controlled by a process scheduler that maximizes the throughput of the workloads through one or more computing platforms without human/user intervention/interaction. In the illustrated embodiment, system 300 includes a host 302 such as, but not limited to, client 110 and/or server 140, having a processor unit 310 and a memory 312. In FIG. 3, memory 312 includes a scheduler 314 for scheduling and performing other actions relative to workload processing as discussed below and a knowledge base 316. Scheduler 314 may be implemented in any suitable manner using known techniques that may be hardware-based, software-based, or some combination of both. For example, scheduler 314 may comprise software, logic and/or executable code for performing various functions as described herein (e.g., residing as software and/or an algorithm running on a processor unit, hardware logic residing in a processor or other type of logic chip, centralized in a single integrated circuit or distributed among different chips in a data processing system).

In the illustrated embodiment, a workload may be considered as a loosely coupled object in an object oriented system. For example, a workload may comprise data and the processes needed to process that data. Scheduler 314 utilizes global variables (including information from knowledge base 316) in order to control the scheduling and processing of workloads. Each processing event requires that the data and the processes for that event be available. In the illustrated embodiment, knowledge base 316 comprises a set of rules 320 and processing history data 322. Processing history data 322 may comprise information learned/gained from previous executions/processing of the same data types by the same processes. For example, computing resources needed to process the data include the CPU as well as many other resources (e.g., memory availability, disk input/output (I/O), network I/O, other hardware and operating system resource constraints, etc.). Scheduler 314 "learns" from previous process executions for the same data type by utilizing a simple proxy for the overall throughput of the workload. The throughput for a particular data type may be determined using the following:

$$\text{Throughput (dataType)} = \text{Elapsed time/MB} = \text{CPU time/MB} + \text{Other time/MB}$$

where the "other time" may be the summation of all times required for execution as the result of the availability of other computing resources, and MB is a megabyte of data.

Rules 320 may comprise information or rules that are created and maintained external to the programs/processes acting on the data (e.g., in a separate text file), thereby enabling rules 320 to be readily changed as needed. Rules 320 may comprise information and/or rules that take into account the various types of resources available (e.g., number of CPUs, CPU utilization, disk space requirements, disk I/O, network I/O, etc.), the "throughput" of previous processes of the same type as a predictor for the required resources for the next process of the same type, and data type default assumptions. In some embodiments, rules 320 may be "implementation defined" such as based on a particular data type, user/workload priority, etc. Some example rules 320 may be:

dataTypeP is a heavy CPU utilizer, so only execute a maximum of one process per CPU;

dataTypeT is a light CPU utilizer, so only execute a maximum of five processes per CPU;

dataTypeT is a light CPU utilizer and there are no dataTypeP processes running, so execute a maximum of ten processes CPU; and if userID=xx, then priority is high.

In the illustrated embodiment, system 300 includes one or more computing platforms 330 for performing process operations on workloads. In FIG. 3, three computing platforms $330_1$, $330_2$ and $330_3$ are depicted; however, it should be understood that a greater or fewer quantity of computing platforms 330 may be used. Further, it should be understood that workload processing may also be performed on host 302 using resources available on host 302. Each computing platform 330 may include one or more processor units $332_{1-3}$, a memory $334_{1-3}$ having one or more instances of an operating system $336_{1-3}$ and one or more programs/applications $338_{1-3}$ for performing corresponding processes $340_{1-3}$ on data. In the illustrated embodiment, memory 312 of host 302 may also include resource data 324 comprising information associated with computing resources available for processing workloads (e.g., computing resources of platforms 330).

From an operational perspective, data and processes are "fed" into the system by placing them in "input source" locations. An input source location may comprise a "data source" location and a "process source" location. For example, placing the data and/or processes in input source locations may comprise placing them in input queues (e.g., where each queue contains data or processes of a specific workload type) or placing them in input directories (e.g., where each directory contains data or processes of a specific workload type). Both "input queues" and "input directories" may be considered logically equivalent sources or feeds since in either case the availability of data and/or processes is made known to scheduler 314 by placing the data in a known input location. The processes may also be received in an input queue, thereby enabling a different process to be used for processing the same data type based on some requirement that is determined external to scheduler 314. Also the same process may be used to process the particular data type but the parameters that are submitted along with the process may vary based on the particular instance of the data type. These parameters may be passed as part of a process execution string or passed in as a batch job (e.g., an execution script or its equivalent JCL (Job Control Language) for mainframe execution). In the illustrated embodiment, processes and the programs/application associated with such processes are depicted as residing on particular platforms 330; however, it should be understood that the data and/or processes (e.g., instances of applications/programs for processing the data) may be loaded and/or instantiated on a particular computing platform 330 as such instances become available (e.g., due to licensing constraints, current use on other platforms, etc.).

Scheduler 314 is configured to select data from the appropriate data source for processing based on knowledge base 316 and the available computing resources. Processing of the data may involve running multiple processes that either consume data from multiple sources or use the output of one process as the input to the next process, or a combination of both. In the final step the output data may be placed into a "data destination" (e.g., an output queue or output directory). For example, in the illustrated embodiment, input data 342 may, in response to becoming available for processing, be processed by computing platform $330_1$ via process $340_1$, and the output data 344 of that process, when available, becomes input data 346 to be processed by computing platform $330_2$ via process $340_2$. In turn, output data 348 from process $340_2$ becomes input data 350 to be processed by computing platform $330_3$ via process $340_3$. Output data 352 of process $340_3$ may be provided to another computing platform 330, placed in an output queue or output directory, or otherwise managed/processed. It should be understood that multiple processes may be performed by a single computing platform 330.

Scheduler 314 controls and/or manages workload processing based on when the data is received/available such that the process becomes eligible to proceed when the data is available. Scheduler 314 may initiate a workload processing operation based on rules 320, history data 322, workload/data priority and the computing resources available. When an output from a first process is completed, the next process is then eligible to proceed to process the data. This process may be repeated until the desired output is reached. Processing on multiple platforms 330 is enabled by controlling the input and output data and/or process locations, thereby enabling multiple platforms 330 to be daisy-chained or linked together for workload processing. In some embodiments, a data push scenario may be utilized (e.g., output data from one computing platform 330 is transmitted to another computing platform 330 for further processing). The determination of which platform 330 to transmit to can be predetermined based on data type, predetermined based on process type, based on a round robin type rule. In some embodiments, a data pull scenario may be utilized (e.g., the final output data may remain on one computing platform 330 while other computing platform(s) 330 may poll the first platform 330 for data availability as resource availability permits). For example, the output data 344 may remain on platform $330_1$ and platforms $330_2$ and $330_3$ may poll platform $330_1$ for data availability as resources on the respective platforms $330_2$ and $330_3$ become available (i.e., whichever of the two platforms $330_2$ and $330_3$ is least busy will pick-up the data from platform $330_1$).

Figure 4:
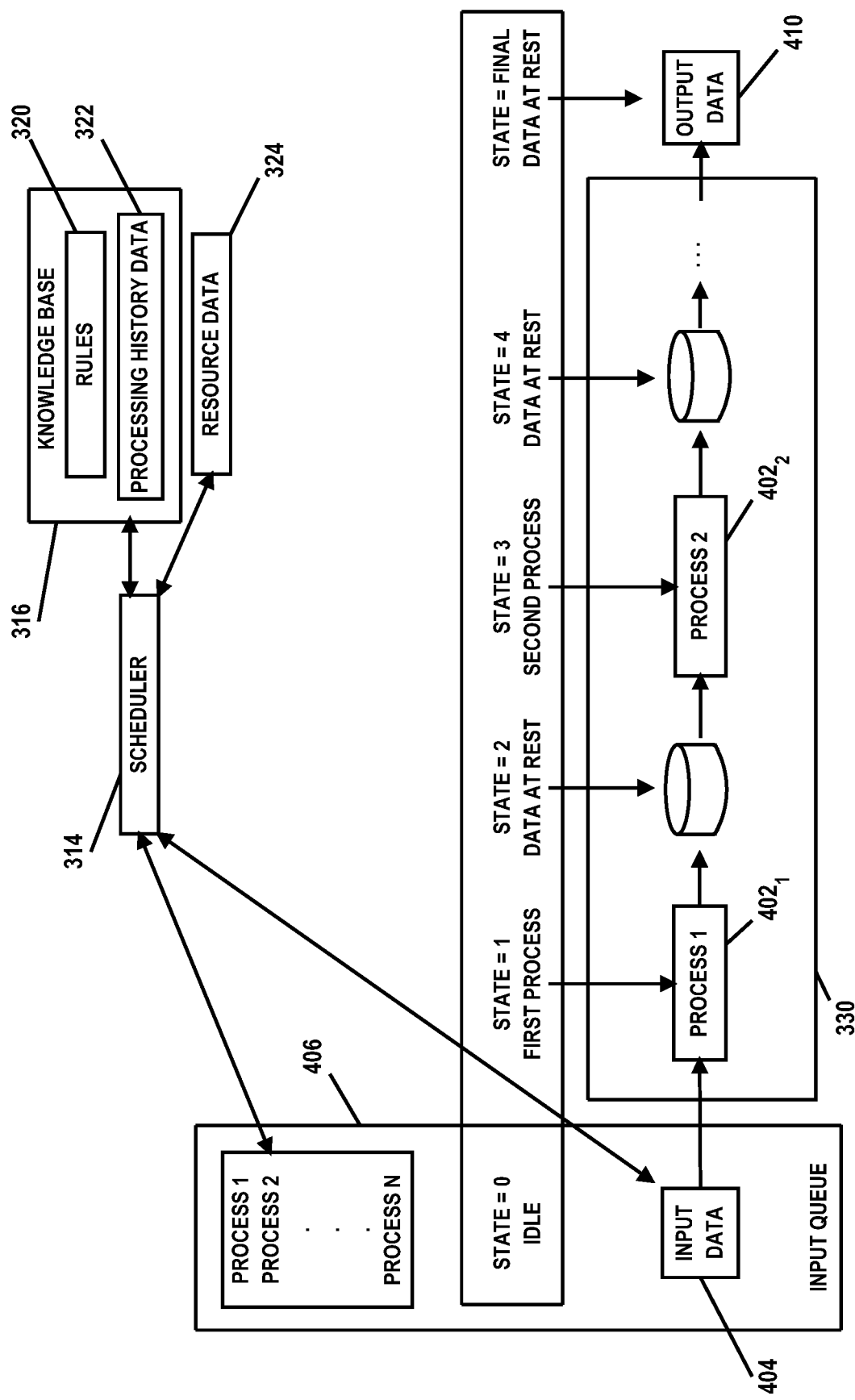
FIG. 4 is a diagram illustrating an embodiment of cross-platform workload processing according to the present disclosure.

FIG. 4 is a diagram illustrating an embodiment of cross-platform workload processing according to the present disclosure. In the illustrated embodiment, a batch migration is depicted where a large repository (e.g., multiple terabytes or greater) of data is to be migrated from one archive/storage system to another (or from one media type or computing platform to another). The migration process is achieved by creating and executing thousands through tens of thousands of batch jobs (in this example, each batch job is a script that initiates a single process). In this example, the processing of the data passes through multiple states. There are two general states (e.g., a state in which the data is "at rest" (e.g., ready, residing on disk) and a second general state when a process is running against the data to produce an output dataset). In this example, a single input data set goes through multiple processing steps before the final output is produced. Each of these processing steps utilizes different resources based on the functionality of the process (e.g., a compression process would consume mainly CPU and memory while a file transfer process would consume mainly network bandwidth). There are multiple of these processes executing concurrently. Scheduler 314 selects which processes to activate/initiate based on data and process availability as well as system resource availability and process performance based on historical data collection.

In the illustrated example, multiple processes 402 may need to be performed on input data 404 during the migration process. Each process 402 may be performed on a different computing platform 330 or multiple processes 402 may be performed on a single platform 330, or some combination thereof. Scheduler 314 controls/manages the workload processing through a series of operations. Scheduler 314 may first determine whether and/or wait for data 404 and its associated process (e.g., process 1 $402_1$) to become available at a source (e.g., an input queue 406). In response to data 404 and processes $402_1$ becoming available for input, scheduler 314 observes and/or otherwise determines any currently executing workloads and the available computing resources (e.g., resource data 324) of computing platform(s) 330. If excess resource capacity is available, scheduler 314 examines knowledge base 316 and decides if the available workload (e.g., data 404 and process $402_1$) can be run at this time without over-utilizing (degrading) any of the computing resources on platform(s) 330. If so, scheduler 314 selects the data 404 and the corresponding resource (e.g., one or more of platforms 330) for execution of the workload and initiates the processing of the workload on the selected resource (e.g., state 1). At state 2, process $402_1$ has been completed and the processed data may reside on a disk/storage resource or be otherwise at rest awaiting a next processing operation (e.g., in an output queue or output directory). The above process is then repeated by scheduler 314 at states 3 for a process $402_2$, and state 4 through state N, until data 404 has completed its final processing operations, where output data 410 may be stored and/or further managed. Further, scheduler 314 determines and/or otherwise obtains the processing/execution statistics associated with workload processing and updates processing history data 322 (e.g., based on the data type, process, etc.).

Figure 5:
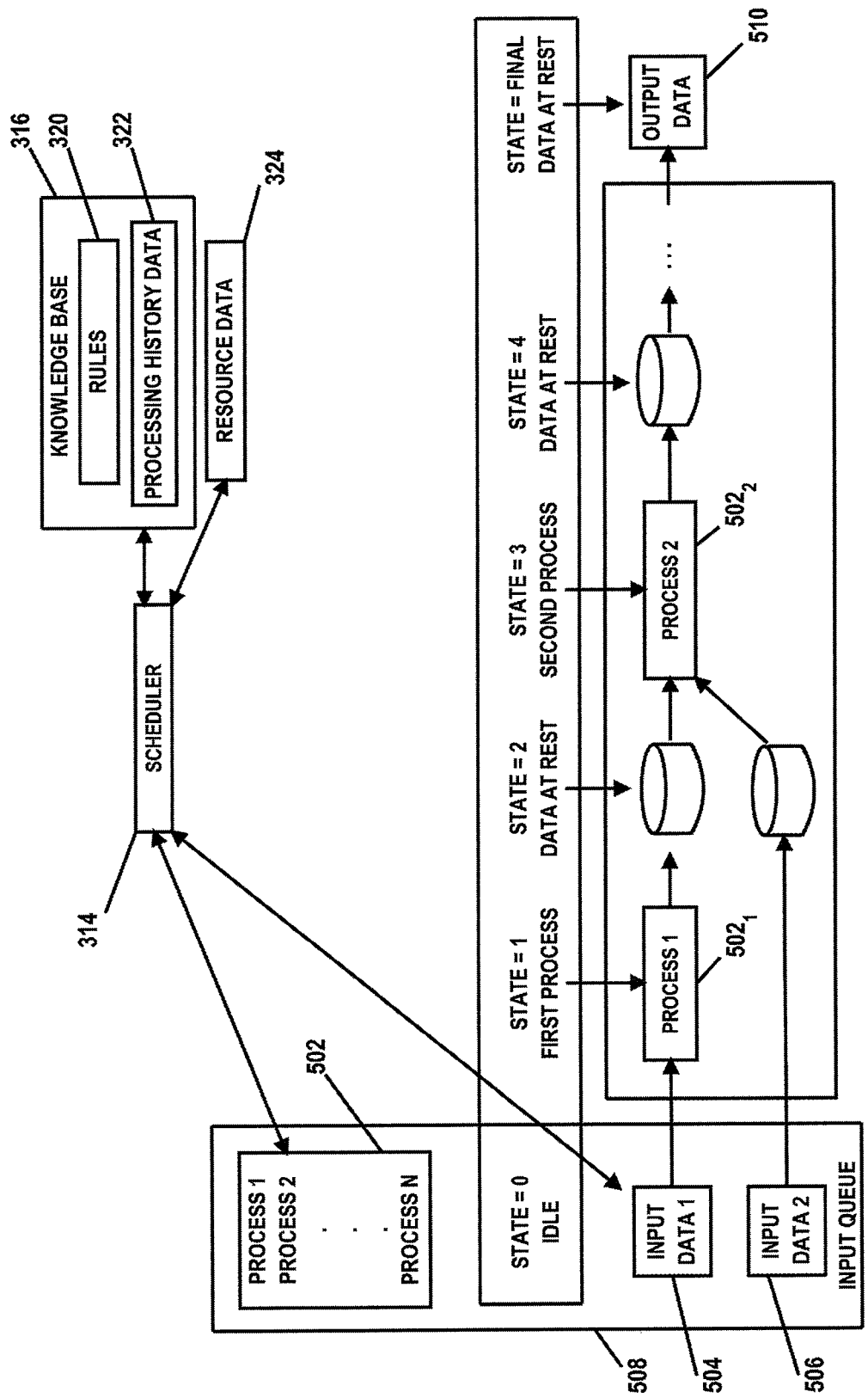
FIG. 5 is a diagram illustrating another embodiment of cross-platform workload processing according to the present disclosure.

FIG. 5 is a diagram illustrating another embodiment of cross-platform workload processing according to the present disclosure. In this embodiment, multiple dataset processing where streams of input data may be continually processed is depicted. In this example, rules 320 may be setup/configured to select which of the input data streams would be processed first, second, etc. This prioritization may be based on data type, data and process availability, or any other rule defined for the environment. In this example, one or more processes 502 require input from two or more datasets. For example, in the illustrated embodiment, input data 504 will be processed via a process $502_1$. Scheduler 314 will wait until all the needed datasets are available for process $502_2$ (e.g., input data 506 and input data 504 that has been processed via process $502_1$) before process $502_2$ becomes eligible to proceed. In response to input data 504 becoming available after process $502_1$ and input data 506 being available, along with the program/process $502_2$, scheduler 314 will initiate the workload processing operation (e.g., process $502_2$) process based on information in knowledge base 316 and resource availability (e.g., using resource data 324). Further processing of workloads through various states or stages may be as set forth above.

Thus, in operation, rules 320 are used to determine which workload (input data and process) is to be processed next. The rules 320 are used to select the data based on the availability of the workload (processes and data) and on a priority determined by knowledge base 316. Scheduler 314 waits for the arrival and/or availability of processes and their related data. Once both the process and its data are available, the workload is eligible to be submitted/initiated/processed. Rules 320 may also be used to determine the priority of the workload submission. The availability of processing/execution resources determines when the workload is executed. Each dataset/input data may go through various independent but sequentially related processes before the final output is produced, and multiple datasets may be included within a single processing operation. Scheduler 314 controls the intermediate processing operations, the combining of datasets for processing when needed, and the combining of the output of different processes into the input for another, subsequent process. Scheduler 314 also manages/controls workload processing across computing platforms of varying technologies (e.g., different types of operating systems, different data formats, etc.).

Figure 6:
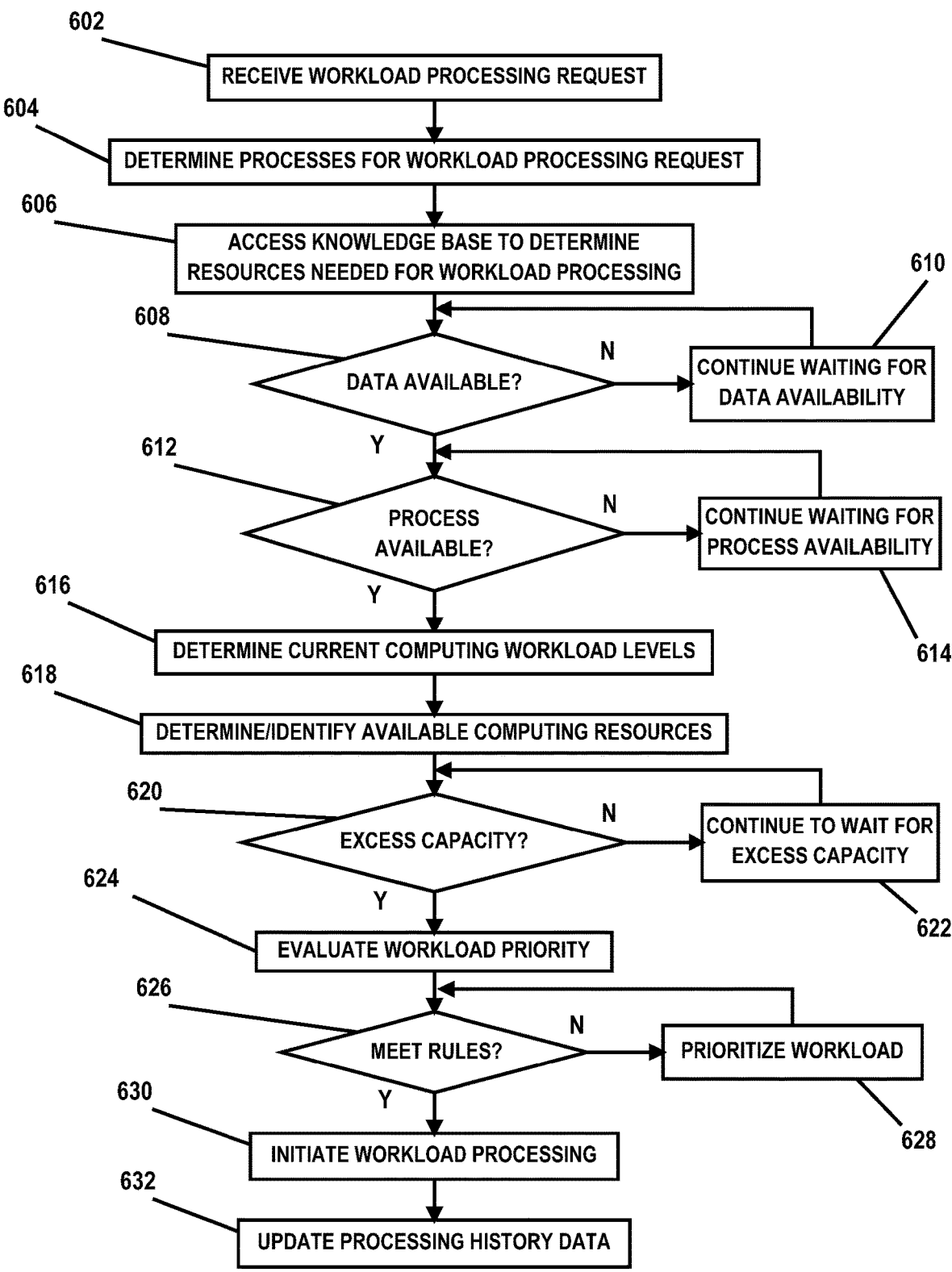
FIG. 6 is a flow diagram illustrating an embodiment of a method for cross-platform workload processing according to the present disclosure.

FIG. 6 is a flow diagram illustrating an embodiment of a method for cross-platform workload processing according to the present disclosure. The method begins at block 602, where scheduler 314 receives a workload processing request (e.g., a request to migrate data from one platform to another, from one data type to another, etc.). At block 604, scheduler 314 may determine needed processes for the workload processing. For example, scheduler 314 may access knowledge base 316 to determine the types of processes for processing the workload (e.g., data compression or extraction, translation, etc.). At block 606, scheduler 314 may accesses knowledge base 316 to determine computing resources needed for processing the workload. For example, scheduler 314 may access rules 320 or other types of information in knowledge base to identify a particular program/application/process (or processes needed at various stages of processing the workload) (e.g., compression process, followed by a translation process, etc.). At decisional block 608, scheduler 314 determines whether the data corresponding to the workload is available (e.g., available at a particular source, queue or directory). If not, the method proceeds to block 610, where scheduler 314 may continue to monitor for the availability of the workload data.

In response to the data becoming available, the method proceeds from decisional block 608 to decisional block 612, where scheduler 314 determines whether the process for the workload is available. If not, the method proceeds to block 614, where scheduler 314 may continue to monitor for the availability of the process. In response to the process becoming available, the method proceeds from decisional block 612 to block 616, where scheduler 314 observes current computing processing levels (e.g., current workload processing levels of computing platforms 330). At block 618, scheduler 314 determines and/or otherwise identifies available computing resources for the workload processing on computing platforms 330 (e.g., accessing and/or reviewing resource data 324 or otherwise communicating with computing platforms 330 to assess current processing levels). At decisional block 620, scheduler 314 determines whether excess capacity exists on one or more computing platforms 330 for processing the workload. For example, scheduler 314 may access knowledge base 316 (e.g., processing history data 322) to determine a number of CPUs, memory capacity, etc., needed for processing the workload to ensure resources of the computing platform are not over-utilized. If insufficient capacity is determined, the method proceeds to block 622, where scheduler 314 may continue to monitor processing levels of the available computing platforms.

If excess capacity is identified at decisional block 620, the method proceeds to block 624, where scheduler 314 may access rules 320 for evaluating a priority of the workload relative to other workloads needing to be processed. At decisional block 626, scheduler 314 determines whether initiating processing of the workload complies with rules 320 (e.g., priority levels, needed resources, etc.). If not, the method proceeds to block 628, where scheduler 314 may prioritize the workload according to rules 320. If a determination is made at decisional block 626 that the workload meets the priority requirement or that the priority of the workload is such that it exceeds other waiting workloads, the method proceeds to block 630, where scheduler 314 initiates and/or otherwise causes execution of the workload processing using the selected computing platform. At block 632, scheduler 314 access processing statistics associated with the processing of the workload (e.g., throughput information, memory capacity utilized, etc.) and updates processing history data 324.

Thus, embodiments of the present disclosure enable workload throughput optimization using a knowledge base to evaluate throughput information obtained from previous, similar workload processing to efficiently schedule and manage workload processing across one or more computing platforms. A set of rules may be set/used to determine which workload (input data and process) is to be processed next, the availability of the workload, and a priority determined by the knowledge base. A scheduler waits for the arrival/availability of processes and their related data and, in response to the data and its associated process(es) having arrived or otherwise being available, the workload is eligible to be submitted according to a priority of the workload (e.g., as set forth by the rules) and the availability of processing/execution resources. The scheduler controls/manages intermediate processing stages of the workload without user intervention based on the workload being available for processing as well as computing resource availability.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method, comprising:
  receiving a request to process a workload by a scheduler executing on a processor unit;
  determining, from a knowledge base, that multiple stages of processing are needed to process data of a workload indicated in the workload processing request;
  responsive to determining that multiple stages of processing are needed:
    determining a process needed for each stage of the multiple stages;
    determining, from the knowledge base, a throughput value associated with previous processing requests for a corresponding type of the workload; and
    predicting, based on the throughput value, resources needed for each stage of the multiple stages;
  determining, at the respective stage, available resources based on currently executing workloads of a plurality of computing platforms;
  determining, based upon the predicted resources needed for the respective stage and the available resources, that a computing platform of the plurality of computing platforms has excess capacity sufficient for processing the workload;
  accessing, at the respective stage, a set of rules for evaluating a priority of the workload relative to other workloads and to determine limitations on a quantity of processes to execute per resource;
  allocating select ones of the available resources for the processing of the workload at the respective stage, the allocating based on the throughput value; and initiating processing of the workload for the respective stage on the computing platform utilizing the select ones of the available resources according to the set of rules.

2. The method of claim 1, further comprising determining workload processing statistics of the workload processing.

3. The method of claim 1, further comprising determining a data type of the workload.

4. The method of claim 1, further comprising: determining that the data for the respective stage is available; and instantiating the process at the respective stage on the computing platform in response to the data for the respective stage being available.

5. The method of claim 1, wherein receiving the request comprises: determining a first workload process for the workload, the first workload process processing the data from a first state to a second state; automatically initiating the first workload process on a first computing platform in response to the data in the first state being available to the first computing platform; determining a second workload process for the workload, the second workload process processing the data from the second state to a third state; and automatically initiating the second workload process on a second computing platform in response to the data in the second state being available to the second computing platform.

6. The method of claim 5, further comprising polling, by the second computing platform, the first computing platform to determine whether the data in the second state is available.

7. The method of claim 1, further comprising: determining that the data and the process of the workload are available; and responsive to determining that the data and the process of the workload are available, placing the data and the process each in a respective input queue.

8. The method of claim 1, further comprising determining the throughput value for the type of the workload based on a data type being processed.

9. A method, comprising:
receiving a request to process a workload by a scheduler executing on a processor unit; identifying a plurality of data streams associated with the workload;
determining, from a knowledge base, that multiple stages of processing are needed to process the plurality of data streams;
responsive to determining that multiple stages of processing are needed:
  determining a process needed for each stage of the multiple stages;
  determining, from the knowledge base, a throughput value associated with previous processing requests for a same type of workload processing; and
  predicting, based on the throughput value, resources needed for processing the workload for each stage;
determining, at the respective stage, available resources based on currently executing workloads of a plurality of computing platforms;
determining, based upon the predicted resources needed for the respective stage and the available resources, that a computing platform of the plurality of computing platforms has excess capacity sufficient for processing the workload;
accessing a set of rules for evaluating a priority of the workload relative to other workloads and to determine limitations on a quantity of processes to execute per resource;
selecting a first input data stream from the plurality of data streams to input to a first process according to the priorities defined by the set of rules allocating a first set of resources for the processing of the workload at the first process based on the throughput value;
initiating processing of the first input data stream via the first process; and
selecting a second input data stream from the plurality of data streams to input to a second process according to the priorities defined by set of rules upon completion of the first process.

10. The method of claim 9, further comprising defining the priorities in the set of rules based on the type of data in the respective plurality of data streams.

11. The method of claim 9, further comprising initiating the second process with the second input data stream.

12. The method of claim 9, further comprising inputting the second input data stream with an output data stream of the first process into the second process according to the set of rules.

13. The method of claim 9, further comprising determining workload processing statistics of the workload processing.

14. The method of claim 9, further comprising determining a data type of the workload.

15. The method of claim 9, further comprising determining the throughput value for each type of data of the plurality of data streams.

* * * * *